(12) United States Patent
Li et al.

(10) Patent No.: US 10,598,629 B2
(45) Date of Patent: Mar. 24, 2020

(54) SENSOR AND MEASUREMENT METHOD FOR MEASURING HYDROGEN CONTENT IN METAL MELT

(71) Applicant: Northeastern University, Shenyang, Liaoning Province (CN)

(72) Inventors: Ying Li, Shenyang (CN); Yu shi Ding, Shenyang (CN)

(73) Assignee: NORTHEASTERN UNIVERSITY, Shenyang, Liaoning Province (CN)

( * ) Notice: Subject to any disclaimer, the term of this patent is extended or adjusted under 35 U.S.C. 154(b) by 113 days.

(21) Appl. No.: 15/774,205

(22) PCT Filed: Nov. 30, 2015

(86) PCT No.: PCT/CN2015/096049
§ 371 (c)(1),
(2) Date: May 7, 2018

(87) PCT Pub. No.: WO2017/080005
PCT Pub. Date: May 18, 2017

(65) Prior Publication Data
US 2018/0328881 A1 Nov. 15, 2018

(30) Foreign Application Priority Data

Nov. 12, 2015 (CN) .......................... 2015 1 0770945

(51) Int. Cl.
*G01N 27/411* (2006.01)
*G01N 33/00* (2006.01)
(Continued)

(52) U.S. Cl.
CPC ....... *G01N 27/4114* (2013.01); *G01N 33/005* (2013.01); *G01N 27/30* (2013.01); *G01N 27/301* (2013.01); *G01N 33/2025* (2019.01)

(58) Field of Classification Search
CPC . G01N 33/2025; G01N 27/30; G01N 27/4114
See application file for complete search history.

(56) References Cited

U.S. PATENT DOCUMENTS

2005/0252789 A1 11/2005 Fray et al.
2009/0139876 A1 6/2009 Hills et al.

FOREIGN PATENT DOCUMENTS

CN 101071119 A 11/2007
EP 0544281 B1 6/1998

OTHER PUBLICATIONS

Fukatsu et al., "Hydrogen sensor for molten metals usable up to 1500 K," Solid State Ionics 113-115 (1998) 219-227 (Year: 1998).*

* cited by examiner

*Primary Examiner* — Alexander S Noguerola
(74) *Attorney, Agent, or Firm* — Muncy, Geissler, Olds & Lowe, PC

(57) ABSTRACT

A sensor and a measurement method for measuring hydrogen content in metal melt. The sensor has a solid proton conductor element, a reference electrode, a quasi-electrode to be measured, a reference compound, a through pipe and an insulating ceramic adhesive. The measurement method has the steps of: (1) inserting the sensor and a corrosion-resistant electrode into the metal melt, and making sure that the solid proton conductor element is fully immersed into the metal melt, the quasi-electrode to be measured is in direct contact with the metal melt and the contact surface is the electrode to be measured; (2) connecting a potentiometer and the reference electrode cable or the metal gas guide pipe to the corrosion-resistant electrode, and measuring a potential difference between the reference electrode and the electrode to be measured; and (3) calculating the hydrogen content S of the metal melt.

14 Claims, 9 Drawing Sheets

(51) Int. Cl.
*G01N 33/2025* (2019.01)
*G01N 27/30* (2006.01)

SENSOR AND MEASUREMENT METHOD FOR MEASURING HYDROGEN CONTENT IN METAL MELT

BACKGROUND OF THE INVENTION

1. Field of the Invention

The present invention relates to a hydrogen measurement sensing technology, in particular to a sensor and measurement method for measuring hydrogen content in metal melt.

2. The Prior Arts

In general, hydrogen is a harmful element in metal materials and can cause metal materials to produce defects such as hydrogen embrittlement, porosity and pinholes. Timely measurement of hydrogen content in metals and proper dehydrogenation after information feedback can avoid various hydrogen-induced defects in metal materials. EP0544281 TYK discloses a device for measuring hydrogen content in aluminum melt by a solid proton conductor. The hydrogen content of the metal melt of 1000° C. or below such as aluminum melt can be measured.

Because the solid proton conductor hydrogen sensor can be used for measuring hydrogen content in gas, the reference electrode and the electrode to be measured of the solid proton conductor sensor are both external porous electrodes. A reference substance with certain hydrogen partial pressure is stuffed into the reference electrode, or gas with certain hydrogen partial pressure is introduced, and the electrode to be measured is in contact with atmosphere to be measured, so that a concentration cell is obtained.

The cell reaction is:

$$H_2(high) = H_2(low) \quad (1)$$

$$\Delta G = RT\ln\frac{p_{H_2}^{low}}{p_{H_2}^{high}} = -2EF \quad (2)$$

A potentiometer is used for measuring the electromotive force of the concentration cell. The hydrogen partial pressure of the reference electrode is known (the hydrogen partial pressure of the reference electrode can be higher or lower than that of the electrode to be measured), so that the hydrogen partial pressure of the atmosphere to be measured can be calculated, and the hydrogen content is calculated.

According to a probe and method for measuring hydrogen content disclosed by TYK, a solid proton conductor is used as the main body of the sensor probe, the solid proton conductor and the metal melt are isolated by a ceramic bushing, a ceramic cover or a porous material, and thereof, a gas chamber is created between the proton conductor and the metal melt. The method for measuring hydrogen content in metal melt comprises the following steps of establishing equilibrium hydrogen partial pressure between the metal melt and the gas chamber atmosphere in the sensor probe, and measuring the hydrogen partial pressure according to a Sievert's law:

$$S = k\sqrt{p_{H_2}} \quad (3)$$

in the formula (3), S is the hydrogen content of metal melt, k is a constant, and $p_{H_2}$ is the equilibrium hydrogen partial pressure of the metal melt. At the moment, the hydrogen partial pressure of atmosphere in a porous material is equilibrium hydrogen partial pressure of the metal melt, and the hydrogen content in the aluminum melt can be obtained through calculation.

US2005/0252789 proposes that a metal-hydrogen material with stable chemical stability such as $\alpha Ti$-$\beta Ti$, $\alpha Zr$-$\beta Zr$ and $\alpha Hf$-$\beta Hf$ is taken as the reference substance of the sensor. The interface between the reference substance and the solid electrode can maintain chemical stability at higher temperature, influence of oxygen on the solid proton conductor is reduced, and stable hydrogen partial pressure is provided. However, the patent does not refer to the measurement method of hydrogen content in detail.

US2009/0139876 discloses a device for measuring hydrogen content in metal melt by using a solid proton conductor and proposes a method for restoring the solid electrolyte of the proton conductor by using a water absorbing material such as AlN and BN.

According to the device and the method, the equilibrium hydrogen partial pressure established between the metal melt and the gas chamber in the probe is measured by using the hydrogen concentration cell of the solid proton conductor. The method has the following disadvantages that: (1) time for establishing equilibrium between the metal melt and the gas chamber is long, which results in low sensor response speed; (2) the material for establishing the gas chamber in the sensor is usually the ceramic cover or fiber materials, water is easy to adhere to the surfaces of such materials, water reacts with the metal melt to produce a large amount of hydrogen during measurement, and the accuracy of measurement results is affected; and (3) during multiple measurement processes, the gas chamber is easy to block by metal and metal oxides adhered to the surface of the probe, so that establishment of equilibrium is slow, response speed is reduced and even measurement accuracy is affected.

SUMMARY OF THE INVENTION

In accordance with the problems existing in the prior art, the present invention provides a sensor and measurement for measuring hydrogen content in metal melt. A proton conductor in the sensor is in direct contact with the metal melt to form an electrode to be measured. It is not necessary to establish hydrogen solubility equilibrium with the metal melt via gas for the electrode to be measured, but the proton conductor is adopted to directly establish electrochemical equilibrium between a reference substance and hydrogen in the metal melt.

The present invention adopts the following technical scheme of providing:

a sensor for measuring hydrogen content in metal melt, which comprises a solid proton conductor element, a reference electrode, a quasi-electrode to be measured, a reference substance, a through pipe and an insulating ceramic adhesive, wherein the through pipe and the solid proton conductor element are connected through the insulating ceramic adhesive to form an inner space, the surface located in the space, of the solid proton conductor element, is an inner surface, and the surface exposed outside is an outer surface; the reference electrode is coated to the inner surface of the solid proton conductor element, and the quasi-electrode to be measured is the outer surface of the solid proton conductor element; the quasi-electrode to be measured is in contact with the metal melt during hydrogen measurement, and the contact surface forms the electrode to be measured; and the reference substance is gas-phase reference substance, liquid-phase reference substance or solid-phase reference substance, is placed in the inner space and is in contact with the reference electrode.

The sensor for measuring hydrogen content in metal melt can also comprise a gas guide pipe and a tee fitting. When the reference substance is gas-phase reference substance, the tee fitting is connected with the upper part of the through pipe, the gas guide pipe is inserted into the inner space through the tee fitting and is connected to the reference electrode; when the bottom end of the gas guide pipe directly faces to the reference electrode and the solid proton conductor element, the bottom end of the gas guide pipe is a blind end, a side opening of the gas guide pipe acts as a gas outlet which has the effect of preventing pressure change caused by the gas-phase reference substance rushing at the reference electrode or the proton conductor element and improving measurement accuracy.

The sensor for measuring hydrogen content in metal melt can also comprise a reference electrode cable. When the reference substance is a gas-phase reference substance, the reference electrode cable is inserted into the through pipe through the tee fitting, electrically connected with the reference electrode and externally connected to a measuring circuit; when the reference substance is liquid-phase reference substance or solid-phase reference substance, a reference electrode cable penetrates through the insulating ceramic adhesive, is electrically connected with the reference electrode and is externally connected to the measuring circuit.

The gas guide pipe is made of corundum, quartz, zirconium oxide, stainless steel, nickel-chromium alloy or iron-chromium-aluminum alloy. When the corundum, quartz or zirconium oxide gas guide pipe is used, the sensor comprises a reference electrode cable.

The tee fitting is made of stainless steel, copper, Teflon, nylon or polyurethane.

The reference electrode cable is made of metal platinum, gold, silver, nickel-chromium alloy, iron-chromium-aluminum alloy or stainless steel.

When the reference substance is liquid-phase reference substance or solid-phase reference substance, the sensor for measuring hydrogen content in metal melt comprises an inert material of $Al_2O_3$, YSZ or $Y_2O_3$; and the inert material is stuffed between the reference substance and the insulating ceramic adhesive.

The solid proton conductor element can adopt a tubular, spherical, flaky, discoid, cubic or cylindrical structure and is made of a perovskite or complex perovskite structure material.

The reference electrode is made of silver, platinum or gold.

The insulating ceramic adhesive is an alumina-based material.

The reference substance is gas-phase reference substance, liquid-phase reference substance or solid-phase reference substance, wherein the gas-phase reference substance comprises hydrogen and argon calibration gas mixtures, hydrogen and nitrogen calibration gas mixtures, hydrogen and helium calibration gas mixtures, water vapor and oxygen calibration gas mixtures or ammonia and nitrogen calibration gas mixtures, which is doped or undoped with one or more inert gases, the liquid-phase reference substance comprises lithium and lithium hydride two-phase mixture, and the solid-phase reference substance comprises yttrium hydrogen solid solution, titanium hydrogen solid solution, zirconium hydrogen solid solution or scandium hydrogen solid solution. When the reference substance is liquid-phase reference substance or solid-phase reference substance, the insulating ceramic adhesive is used to seal the reference substance to the side of the reference electrode.

The through pipe is made of corundum, quartz, graphite, stainless steel, Theron, SiC or $LaCrO_3$ and acts as a support and a gas path.

The method for measuring hydrogen content in a metal melt by using the sensor comprises the following process steps of (1) inserting the sensor and a corrosion-resistant electrode into the metal melt, and making sure that the solid proton conductor element is fully immersed into the metal melt, the quasi-electrode to be measured is in direct contact with the metal melt and the contact surface is the electrode to be measured; (2) connecting a potentiometer and the reference electrode cable or the gas guide pipe which is metal to the corrosion-resistant electrode, and measuring potential difference between the reference electrode and the electrode to be measured; and (3) calculating the hydrogen content S of the metal melt according to the measured potential difference, the temperature of the metal melt and the saturated solubility of hydrogen in the metal melt, wherein the cell reaction equation and the calculation formula are shown as (4) and (5):

$$\frac{1}{2}H_2 = [H]_{Metal} \tag{4}$$

one atmospheric pressure and a 1% solution are taken as standard state;

$$\Delta G = \Delta G^\theta + RT \ln \frac{a_{[H]}}{\sqrt{p_{H_2}^{ref}/p^\theta}} = -EF \tag{5}$$

in the formula (5), $\Delta G$ is Gibbs free energy (J/mol); $\Delta G^\theta$ is standard Gibbs free energy (J/mol); R is gas constant (J/(K·mol)); T is thermodynamic temperature (K); a[H] is hydrogen activity; $p_{H_2}^{ref}$ is the hydrogen partial pressure of the reference substance (Pa); pθ is standard pressure (Pa); E is electromotive force (V); and F is Faraday's constant (C/mol).

When equilibrium between hydrogen in the metal melt and hydrogen in the atmosphere is established, the following equation can be obtained:

$$\Delta G = \Delta G^\theta + RT \ln \frac{a_{[H]}}{\sqrt{p_{H_2}^{Gas}/p^\theta}} = 0 \tag{6}$$

in the formula (6), $p_{H_2}^{Gas}$ is the equilibrium hydrogen partial pressure in the atmosphere;

$$a_{[H]} = f_{[H]} \cdot w_{[H]} \tag{7}$$

in the formula (7), $f_{[H]}$ is the activity coefficient of hydrogen in the metal melt, and $w_{[H]}$ is the percentage by mass of hydrogen in the metal melt.

When hydrogen in the metal melt is saturated, the equilibrium hydrogen partial pressure is one standard atmospheric pressure. At the moment, $p_{H_2}^{Gas} = p^\theta$.

$$\Delta G = \Delta G^\theta + RT \ln a_{[H]} = 0 \tag{8}$$

$$\Delta G^\theta = -RT \ln a_{[H]} \tag{9}$$

Because the saturated solubility of hydrogen in most of metals is very low and obeys Henry's law, the activity coefficient $f_{[H]}$ is about 1, $$\Delta G^\theta = -RT \ln w_{[H]} \tag{10}$$

Because hydrogen in the metal melt is saturated, $w_{[H]}$ can be subject to unit transformation by using the saturated solubility of hydrogen and put into the equation;

$$\Delta G^\ominus = -RT \ln KS_0 \quad (11)$$

in the formula (11), $S_0$ is the saturated solubility of hydrogen (ml/100 g), and K is a constant produced by unit transformation. Because the saturated solubility $S_0$ of most of metals is known thermodynamic data or thermodynamic data which can be calculated, the standard Gibbs free energy $\Delta G^\ominus$ for hydrogen dissolving in the metal melt can be calculated.

Because the standard Gibbs free energy $\Delta G^\ominus$ for hydrogen dissolving in the metal melt is only related to the kind and the temperature of the metal melt and does not change along with hydrogen content in the metal melt, when hydrogen is saturated in the metal melt, the standard Gibbs free energy $\Delta G^\ominus$ for hydrogen dissolving in the metal melt is the same as that in unsaturation;

The formula (11) is put into the formula (5) to obtain:

$$\Delta G = RT\ln \frac{KS}{KS_0 \sqrt{p_{H_2}^{ref}/p^\theta}} = -EF \quad (12)$$

$$\ln S = \ln S_0 \sqrt{p_{H_2}^{ref}/p^\theta} - \frac{EF}{RT} \quad (13)$$

$$S = \exp\left(\ln S_0 \sqrt{p_{H_2}^{ref}/p^\theta} - \frac{EF}{RT}\right) \quad (14)$$

The hydrogen content S of the metal melt can be calculated. According to different natures of the selected solid proton conductor and the metal melt to be measured, the formula (14) can be corrected according to experiment results.

The sensor and the measurement method for measuring hydrogen content in metal melt disclosed by the present invention have the beneficial effects as followings:

1. For the sensor for measuring hydrogen content, the proton conductor can be in direct contact with the metal melt, atmosphere of hydrogen equilibrium between the reference substance and the metal melt can be established quickly, the measurement speed is higher, the result is more accurate, the hydrogen measurement sensor is simpler after being simplified, and the hydrogen content of the metal melt of which the temperature is lower than 1000° C. can be measured;

2. In the measurement method for measuring hydrogen content, the hydrogen content in the metal melt is directly calculated according to the potential difference between the hydrogen in the reference substance and hydrogen in the metal melt, the method is more visual and accurate, and the influence of instability of a gas chamber in a conventional sensor on the measurement result is avoided.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Embodiment 1

Figure 1:
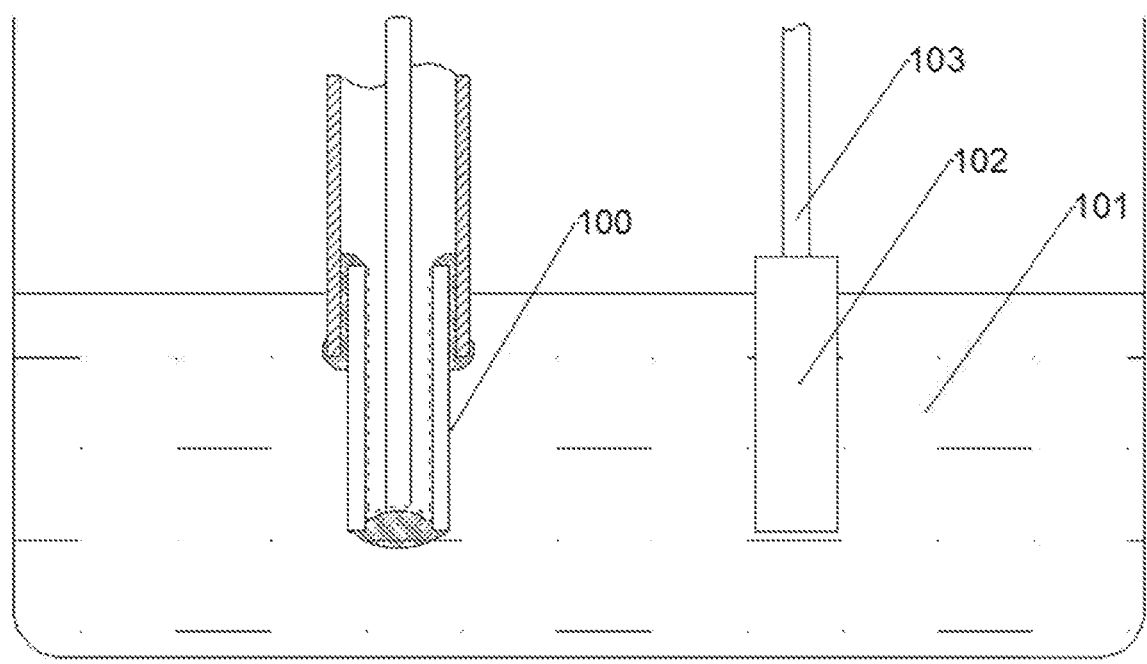
FIG. 1 is the diagram showing the process for measuring hydrogen content in a metal melt by using the sensor of the present invention.
Figure 2:
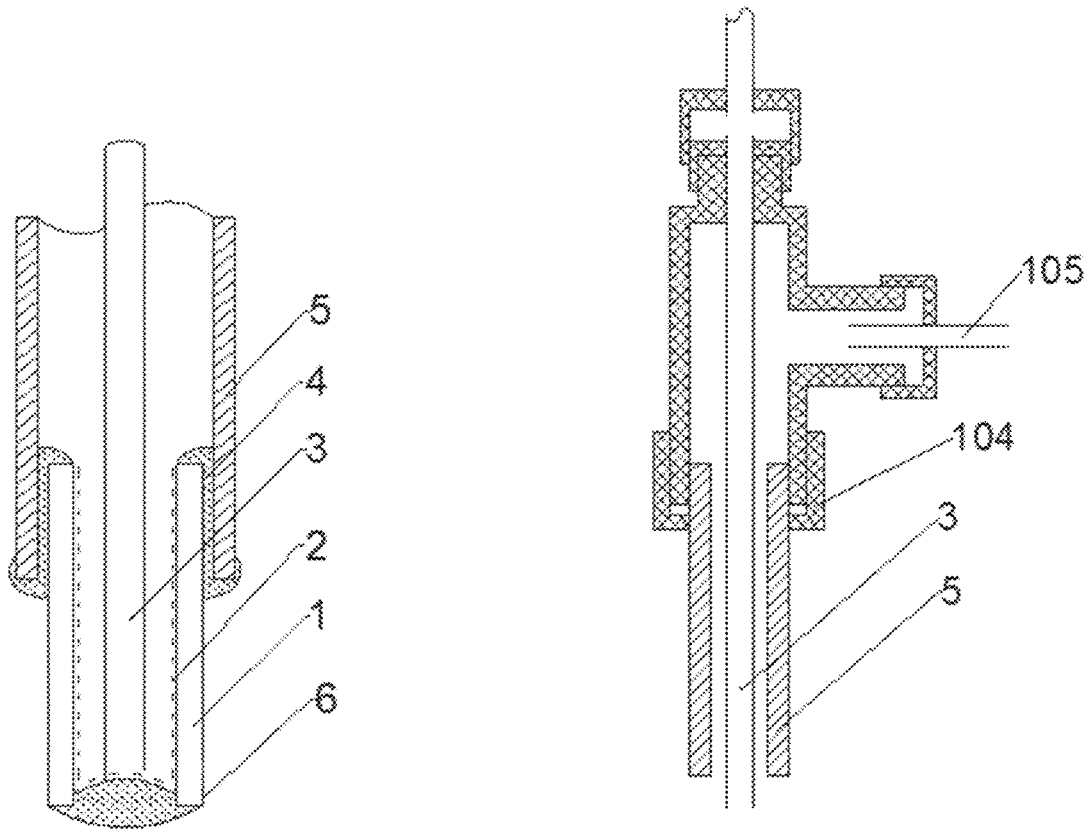
FIG. 2 is the structure diagram of the sensor for measuring hydrogen content in the embodiment 1 of the present invention.

As shown in FIG. 1 and FIG. 2, the sensor for measuring hydrogen content in aluminum melt comprises a $CaZr_{0.9}In_{0.1}O_{3-\alpha}$ solid proton conductor element 1, a reference electrode 2, a quasi-electrode 6 to be measured, a reference substance hydrogen and argon calibration gas mixtures, a stainless steel gas guide pipe 3, a corundum through pipe 5, an alumina-based insulating ceramic adhesive 4 and a Teflon tee fitting 104, wherein the solid proton conductor element 1 adopts a tubular structure and is made of perovskite, one end is sealed by the alumina-based insulating ceramic adhesive 4, the through pipe 5 and the solid proton conductor element 1 are connected through the insulating ceramic adhesive 4 to form an inner space, the surface located in the space, of the solid proton conductor element 1 is an inner surface, and the surface exposed outside is an outer surface; the reference electrode 2 is coated to the inner surface of the solid proton conductor element 1 and the alumina-based insulating ceramic adhesive 4, and the quasi-electrode 6 to be measured is the outer surface of the solid proton conductor element 1; the upper part of the through pipe 5 is connected through the Teflon tee fitting 104, and one side of the Teflon tee fitting 104 is provided with a gas outlet 105; the reference substance hydrogen and argon calibration gas mixtures is introduced into the inner space and is in contact with the reference electrode 2; and the gas guide pipe 3 is inserted into the inner space through the Teflon tee fitting 104 and is in contact with the reference electrode 2.

The reference electrode 2 is made of porous platinum.

For the reference substance hydrogen and argon calibration gas mixtures, the mole hydrogen content is 1.00%.

The method for measuring hydrogen content in a metal melt 101 which is aluminum melt by using the sensor comprises the following process steps of (1) inserting the sensor and a graphite corrosion-resistant electrode 102 into the metal melt 101 which is the aluminum melt of 750° C., and making sure that the solid proton conductor element 1 is fully immersed into the metal melt 101, the quasi-electrode 6 to be measured is in direct contact with the metal melt 101 and the contact surface is the electrode 100 to be measured; (2) connecting a potentiometer and the gas guide pipe 3 to the graphite corrosion-resistant electrode 102 through a stainless steel wire 103, and measuring the potential difference between the reference electrode 2 and the electrode 100 to be measured to be 17.3 mV, wherein the gas guide pipe 3 is metal; and (3) calculating the hydrogen content S of the metal melt 101 according to the measured potential difference, the temperature of the metal melt 101 and the saturated solubility of hydrogen in the metal melt 101, wherein the cell reaction equation and the calculation formula are shown as (4) and (5):

$$\frac{1}{2}H_2 = [H]_{Metal} \quad (4)$$

$$\Delta G = \Delta G^\theta + RT\ln\frac{a_{[H]}}{\sqrt{p_{H_2}^{ref}/p^\theta}} = -EF \quad (5)$$

$$\Delta G^\theta = -RT\ln KS_0 \quad (11)$$

in the formula (11), $S_0$ is the saturated solubility of hydrogen (ml/100 g), and K is a constant produced by unit transformation. Because the saturated solubility $S_0$ of most of metals is known thermodynamic data or thermodynamic data which can be calculated, the standard Gibbs free energy $\Delta G^\theta$ for hydrogen dissolving in the metal melt 101 can be calculated.

Because the standard Gibbs free energy $\Delta G^\theta$ for hydrogen dissolving in the metal melt 101 is only related to the kind and the temperature of the metal melt 101 and does not change along with hydrogen content in the metal melt 101, when hydrogen is saturated in the metal melt 101, the standard free energy $\Delta G^\theta$ for hydrogen dissolving in the metal melt 101 is the same as that in unsaturation;

The formula (11) is put into the formula (5) to obtain:

$$S = \exp\left(\ln S_0\sqrt{p_{H_2}^{ref}/p^\theta} - \frac{EF}{RT}\right) \quad (14)$$

The electromotive force E is measured by the potentiometer, and the stabilized hydrogen content of the aluminum melt is calculated to be S=0.103 ml/100 gAl.

Embodiment 2

Figure 3:
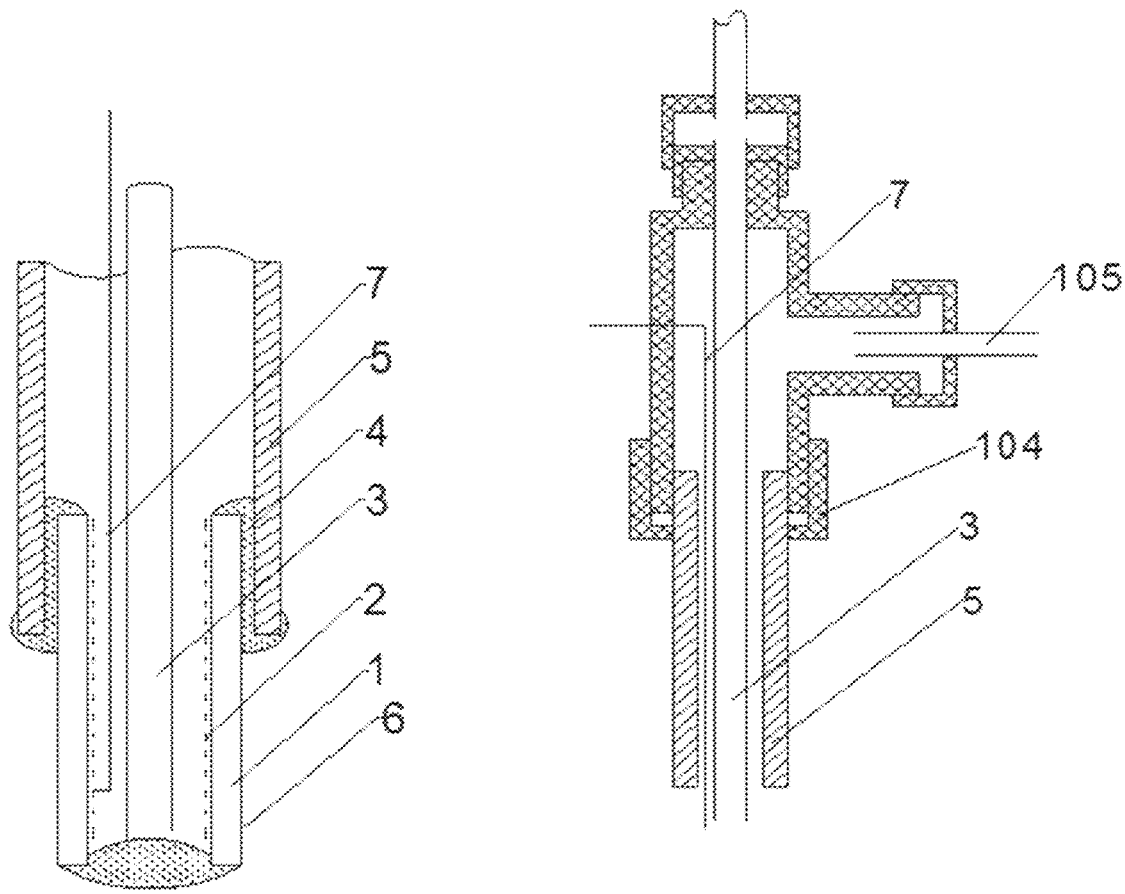
FIG. 3 is the structure diagram of the sensor for measuring hydrogen content in the embodiment 2 of the present invention.

The sensor for measuring hydrogen content in metal melt 101 which is aluminum melt is the same as that in the embodiment 1, as shown in FIG. 3. The difference lies in that: the sensor also comprises a reference electrode cable 7 which is made of metal platinum. The reference electrode cable 7 is inserted into the quartz through pipe 5 through the copper tee fitting 104, is connected to the gold reference electrode 2 and is externally connected to a measuring circuit; the gas guide pipe 3 is made of corundum; the solid proton conductor element 1 is made of $CaZr_{0.9}Sc_{0.1}O_{3-\alpha}$; the tee fitting 104 is made of copper; the through pipe 5 is made of quartz; and the reference electrode 2 is made of porous gold.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the aluminum melt, the quasi-electrode 6 to be measured is in direct contact with the metal melt 101 and the contact surface is the electrode 100 to be measured; (2) connecting a potentiometer and the reference electrode cable 7 to the graphite corrosion-resistant electrode 102 through a platinum wire 103, and measuring the potential difference between the reference electrode 2 and the electrode 100 to be measured; and (3) calculating the stabilized hydrogen content S of the metal melt 101 according to the measured potential difference, the temperature of the metal melt 101 and the saturated solubility of hydrogen in the metal melt 101 to be 0.113 ml/100 gAl.

Embodiment 3

Figure 4:
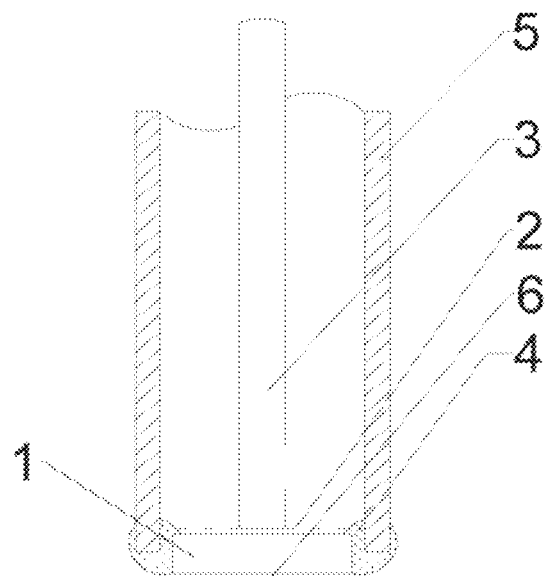
FIG. 4 is the structure diagram of the sensor for measuring hydrogen content in the embodiment 3 of the present invention.

The sensor for measuring hydrogen content in aluminum melt is the same as that in the embodiment 1, as shown in FIG. 4. The difference lies in that: the solid proton conductor element 1 used in the sensor adopts a flaky structure; the through pipe 5 is made of stainless steel; one end being contact with the solid proton conductor element 1, of the nickel-chromium gas guide pipe 3 is a blind end, a side opening of the gas guide pipe 3 is used as a gas outlet, and a vertical distance between the gas outlet and the top end of the solid proton conductor element 1 is 2-5 mm; the gas guide pipe 3 material is made of nickel-chromium alloy; and the reference gas is hydrogen and helium calibration gas mixtures, and the mole hydrogen content is 1.00%.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the aluminum melt, the quasi-electrode 6 to be measured is in direct contact with the metal melt 101 and the contact surface is the electrode 100 to be measured; (2) connecting a potentiometer and the nickel-chromium gas guide pipe 3 to the graphite corrosion-resistant electrode 102 through a nickel-chromium wire 103, and measuring the potential difference between the reference electrode 2 and the electrode 100 to be measured; and (3) calculating the stabilized hydrogen content S of the aluminum melt according to the measured potential difference, the temperature of the metal melt 101 and the saturated solubility of hydrogen in the metal melt 101 to be 0.109 ml/100 gAl.

Embodiment 4

Figure 5:
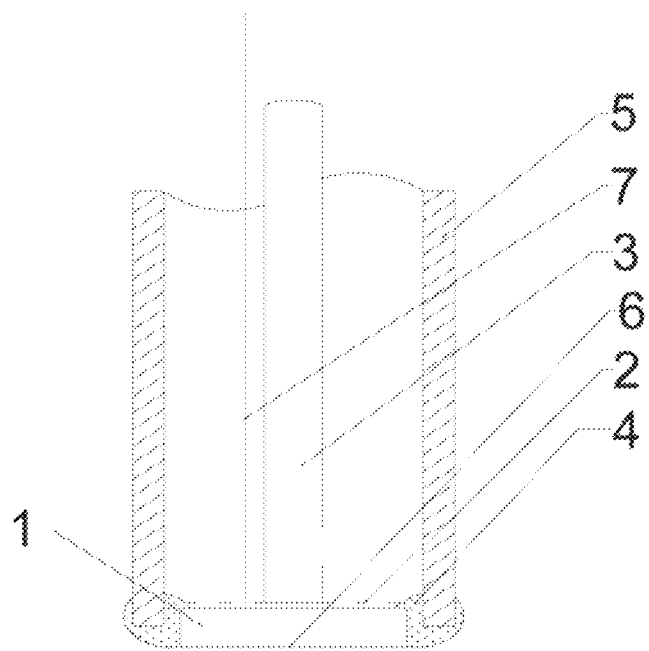
FIG. 5 is the structure diagram of the sensor for measuring hydrogen content in the embodiment 4 of the present invention.

The sensor for measuring hydrogen content in aluminum melt is the same as that in the embodiment 3, as shown in FIG. 5. The difference lies in that: the sensor also comprises a reference electrode cable 7 which is made of metal silver. The reference electrode cable 7 is inserted into the through pipe 5 through the stainless steel tee fitting 104, is connected with the silver reference electrode 2 and is externally connected to a measuring circuit; the through pipe 5 is made of quartz; the gas guide pipe 3 is made of corundum; the reference electrode 2 is made of porous silver; and the reference gas is hydrogen and nitrogen calibration gas mixtures, and the mole hydrogen content is 1.00%.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the metal melt 101, the quasi-electrode 6 to be measured is in direct contact with the metal melt 101 and the contact surface is the electrode 100 to be measured; (2) connecting a potentiometer and the reference electrode cable 7 to the graphite corrosion-resistant electrode 102 through a silver wire 103, and measuring the potential difference between the reference electrode 2 and the electrode 100 to be measured; and (3) calculating the stabilized hydrogen content S of the aluminum melt according to the measured potential difference, the temperature of the metal melt 101 and the saturated solubility of hydrogen in the metal melt 101 to be 0.130 ml/100 gAl.

Embodiment 5

Figure 6:
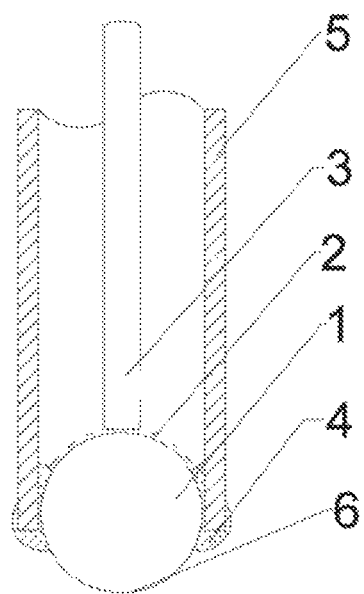
FIG. 6 is the structure diagram of the sensor for measuring hydrogen content in the embodiment 5 of the present invention.

The sensor for measuring hydrogen content in aluminum melt is the same as that in embodiment 3, as shown in FIG. 6. The difference lies in that: the solid proton conductor element 1 used in the sensor adopts a spherical structure.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the aluminum melt, the quasi-electrode 6 to be measured is in direct contact with the metal melt 101 and the contact surface is the electrode 100 to be measured; (2) connecting a potentiometer and the gas guide pipe 3 to the graphite corrosion-resistant electrode 102 through a stainless steel wire 103, and measuring the potential difference between the reference electrode 2 and the electrode 100 to be measured; and (3) calculating the stabilized hydrogen content S of the aluminum melt according to the measured potential difference, the temperature of the metal melt 101 and the saturated solubility of hydrogen in the metal melt 101 to be 0.123 ml/100 gAl.

Embodiment 6

Figure 7:
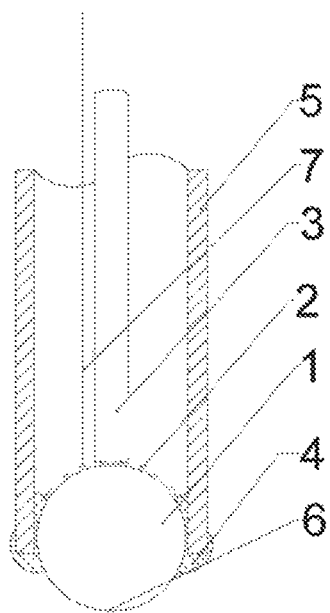
FIG. 7 is the structure diagram of the sensor for measuring hydrogen content in the embodiment 6 of the present invention.

The sensor for measuring hydrogen content in aluminum melt is the same as that in embodiment 5, as shown in FIG. 7. The difference lies in that: the sensor also comprises a reference electrode cable 7 which is made of stainless steel. The reference electrode cable 7 is inserted into the through pipe 5 through the Teflon tee fitting 104, is connected to the reference electrode 2 and is externally connected to a measuring circuit; and the gas guide pipe 3 is made of corundum.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the aluminum melt, the quasi-electrode 6 to be measured is in direct contact with the metal melt 101 and the contact surface is the electrode 100 to be measured; (2) connecting a potentiometer and the reference electrode cable 7 to the corrosion-resistant electrode 102 through a stainless steel wire 103, and measuring the potential difference between the reference electrode 2 and the electrode 100 to be measured; and (3) calculating the stabilized hydrogen content S of the aluminum melt according to the measured potential difference, the temperature of the metal melt 101 and the saturated solubility of hydrogen in the metal melt 101 to be 0.099 ml/100 gAl.

Embodiment 7

Figure 8:
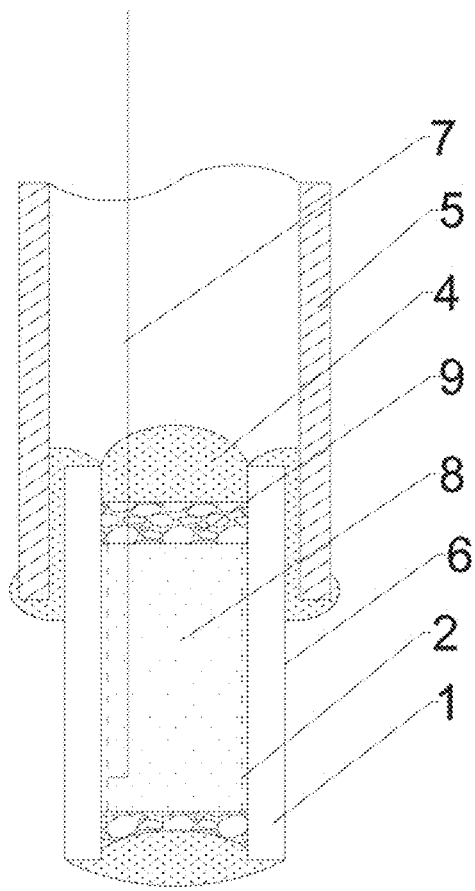
FIG. 8 is the structure diagram of the sensor for measuring hydrogen content in the embodiment 7 of the present invention.

As shown in FIG. 8, the sensor for measuring hydrogen content in aluminum melt comprises a solid proton conductor element 1, a reference electrode 2, an quasi-electrode 6 to be measured, a platinum-wire cable 7, a solid-phase reference substance 8, a corundum through pipe 5, an alumina-based ceramic adhesive 4 and an $Al_2O_3$ inert material 9, wherein the solid proton conductor element 1 adopts a tubular structure and is made of $CaZr_{0.9}In_{0.1}O_{3-\alpha}$, one end is sealed by using the alumina-based ceramic adhesive 4, the through pipe 5 and the solid proton conductor element 1 are connected through the insulating ceramic adhesive 4 to form an inner space, the surface located in the inner space, of the solid proton conductor element 1 is an inner surface, and the surface exposed outside is an outer surface; the reference electrode 2 is coated to the inner surface of the solid proton conductor element 1, and the quasi-electrode 6 to be measured is the outer surface of the solid proton conductor element 1; the bottom of the solid proton conductor element 1 is stuffed with the $Al_2O_3$ inert material 9, the upper part is stuffed with the yttrium hydrogen solid solution system solid-phase reference substance 8, the reference substance 8 is in contact with the reference electrode 2 and the platinum-wire cable 7, the $Al_2O_3$ inert material 9 is stuffed to a space above the reference substance 8, and then the reference substance 8 is sealed by using the alumina-based ceramic adhesive 4 and is connected with the corundum through pipe 5; and the platinum-wire cable 7 penetrates through the insulating ceramic adhesive 4, is connected with the reference electrode 2 and is externally connected to a measuring circuit.

The reference electrode 2 is made of platinum.

The reference substance 8 is a yttrium hydrogen solid solution system solid, and the mole hydrogen content in equilibrium atmosphere of the yttrium hydrogen solid solution system solid at 750° C. is 0.11%.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the metal melt 101, the quasi-electrode 6 to be measured is in direct contact with the metal melt 101 and the contact surface is the electrode 100 to be measured; (2) connecting a potentiometer and a platinum-wire cable 7 to the graphite corrosion-resistant electrode 102 through a platinum wire 103, and measuring the potential difference between the reference electrode 2 and the electrode 100 to be measured; and (3) calculating the stabilized hydrogen content S of the aluminum melt according to the measured potential difference, the temperature of the metal melt 101 and the saturated solubility of hydrogen in the metal melt 101 to be 0.107 ml/100 gAl.

Embodiment 8

Figure 9:
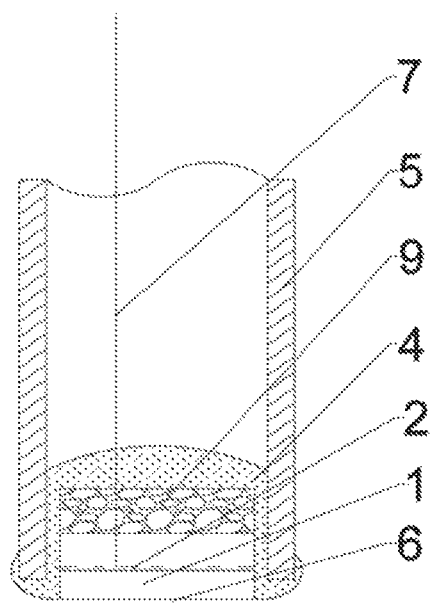
FIG. 9 is the structure diagram of the sensor for measuring hydrogen content in the embodiment 8 of the present invention.

The sensor for measuring hydrogen content in aluminum melt is the same as that in the embodiment 7, as shown in FIG. 9. The difference lies in that: the solid proton conductor element 1 used in the sensor adopts a flaky structure and is made of $CaZr_{0.9}Sc_{0.1}O_{3-\alpha}$; the inert material 9 is $Y_2O_3$; the reference substance is a scandium hydrogen solid solution system solid, and the mole hydrogen content in equilibrium atmosphere of the scandium hydrogen solid solution system solid at 750° C. is 0.25%.

The method for measuring hydrogen content in metal melt 101 by using the sensor comprises the following process steps of (1) inserting the sensor and a graphite corrosion-resistant electrode 102 into the aluminum melt of 750° C., and making sure that the solid proton conductor element 1 is fully immersed into the aluminum melt, the quasi-electrode 6 to be measured is in direct contact with the metal melt 101 and the contact surface is the electrode 100 to be measured; (2) connecting a potentiometer and a cable 7 to the graphite corrosion-resistant electrode 102 through a platinum wire 103, and measuring the potential difference between the reference electrode 2 and the electrode 100 to be measured; and (3) calculating the stabilized hydrogen content S of the aluminum melt according to the measured potential difference, the temperature of the metal melt 101 and the saturated solubility of hydrogen in the metal melt 101 to be 0.143 ml/100 gAl.

What is claimed is:

1. A sensor for measuring hydrogen content in metal melt, comprising: a solid proton conductor element, a reference electrode, a quasi-electrode to be measured, a reference substance, a through pipe and an insulating ceramic adhesive;
    wherein the through pipe and the solid proton conductor element are connected through the insulating ceramic adhesive to form an inner space, the surface located in the space, of the solid proton conductor element, is an inner surface, and the surface exposed outside, of the solid proton conductor element, is an outer surface; the reference electrode is coated to the inner surface of the solid proton conductor element, and the quasi-electrode to be measured is the outer surface of the solid proton conductor element; the quasi-electrode to be measured is in contact with the metal melt during hydrogen measurement, and the contact surface forms the electrode to be measured; and the reference substance is gas-phase reference substance, liquid-phase reference substance or solid-phase reference substance, is placed in the inner space and is in contact with the reference electrode; and
    wherein the sensor further comprises a gas guide pipe and a tee fitting, and when the reference substance is gas-phase reference substance, the tee fitting is connected with an upper part of the through pipe, the gas guide pipe is inserted into the inner space through the tee fitting and is connected to the reference electrode, and when a bottom end of the gas guide pipe directly faces to the reference electrode and the solid proton conductor element, the bottom end of the gas guide pipe is a blind end, a side opening of the gas guide pipe acts as a gas outlet.

2. The sensor for measuring hydrogen content in metal melt according to claim 1, wherein the sensor further comprises a reference electrode cable, and when the reference substance is gas-phase reference substance, the reference electrode cable is inserted into the through pipe through the tee fitting, is connected with the reference electrode and is externally connected to a measuring circuit, and the reference electrode cable is metal platinum, gold, silver, nickel-chromium alloy, iron-chromium-aluminum alloy or stainless steel.

3. The sensor for measuring hydrogen content in metal melt according to claim 1 wherein the solid proton conductor element has a tubular, spherical, flaky, discoid, cubic or cylindrical structure and is made of a perovskite or complex perovskite structure material.

4. The sensor for measuring hydrogen content in metal melt according to claim 1, wherein a material of the reference electrode is silver, platinum or gold.

5. The sensor for measuring hydrogen content in metal melt according to claim 1, wherein a material of the insulating ceramic adhesive is an alumina-based material.

6. The sensor for measuring hydrogen content in metal melt according to claim 1, wherein when the reference substance is gas-phase reference substance, liquid-phase reference substance or solid-phase reference substance, the gas-phase reference substance comprises hydrogen and argon calibration gas mixtures, hydrogen and nitrogen calibration gas mixtures, hydrogen and helium calibration gas mixtures, water vapor and oxygen calibration gas mixtures or ammonia and nitrogen calibration gas mixtures, which is doped or undoped with one or more inert gases, the liquid-phase reference substance comprises lithium and lithium hydride two-phase mixture, and the solid-phase reference substance comprises yttrium hydrogen solid solution, titanium hydrogen solid solution, zirconium hydrogen solid solution or scandium hydrogen solid solution.

7. A method for measuring hydrogen content in metal melt by using the sensor for measuring hydrogen content in metal melt according to claim 1, the method comprising the following steps of:
    (1) inserting the sensor and a corrosion-resistant electrode into the metal melt, and making sure that the solid proton conductor element is fully immersed into the metal melt, the quasi-electrode to be measured is in direct contact with the metal melt and the contact surface is the electrode to be measured;
    (2) connecting a potentiometer and the gas guide pipe to the corrosion-resistant electrode, and measuring a potential difference between the reference electrode and the electrode to be measured, wherein the gas guide pipe is metal, when the reference substance is gas-phase reference substance, the tee fitting is connected with an upper part of the through pipe, the gas guide pipe is inserted into the inner space through the tee fitting and is connected to the reference electrode, and when a bottom end of the gas guide pipe directly faces to the reference electrode and the solid proton conductor element, the bottom end of the gas guide pipe is a blind end, a side opening of the gas guide pipe acts as a gas outlet; and
    (3) calculating the hydrogen content S of the metal melt according to the measured potential difference, a temperature of the metal melt and a saturated solubility of hydrogen in the metal melt.

8. A sensor for measuring hydrogen content in metal melt, comprising: a solid proton conductor element, a reference electrode, a quasi-electrode to be measured, a reference substance, a through pipe and an insulating ceramic adhesive;
    wherein the through pipe and the solid proton conductor element are connected through the insulating ceramic adhesive to faun an inner space, the surface located in the space, of the solid proton conductor element, is an inner surface, and the surface exposed outside, of the solid proton conductor element, is an outer surface; the reference electrode is coated to the inner surface of the solid proton conductor element, and the quasi-electrode to be measured is the outer surface of the solid proton conductor element; the quasi-electrode to be measured is in contact with the metal melt during hydrogen measurement, and the contact surface forms the electrode to be measured; and the reference substance is gas-phase reference substance, liquid-phase reference substance or solid-phase reference substance, is placed in the inner space and is in contact with the reference electrode; and wherein the sensor comprises a reference electrode cable, wherein when the reference substance is liquid-phase reference substance or solid-phase reference substance, the reference electrode cable penetrates through the insulating ceramic adhesive, is connected with the reference electrode and is externally connected to a measuring circuit, and the reference electrode cable is metal platinum, gold, silver, nickel-chromium alloy, iron-chromium-aluminum alloy or stainless steel.

9. The sensor for measuring hydrogen content in metal melt according to claim 8, wherein when the reference substance is liquid-phase reference substance or solid-phase reference substance, the sensor further comprises an inert material of $Al_2O_3$, YSZ or $Y_2O_3$; and the inert material is stuffed between the reference substance and the insulating ceramic adhesive.

10. The sensor for measuring hydrogen content in metal melt according to claim 8, wherein the solid proton conductor element has a tubular, spherical, flaky, discoid, cubic or cylindrical structure and is made of a perovskite or complex perovskite structure material.

11. The sensor for measuring hydrogen content in metal melt according to claim 8, wherein a material of the reference electrode is silver, platinum or gold.

12. The sensor for measuring hydrogen content in metal melt according to claim 8, wherein a material of the insulating ceramic adhesive is an alumina-based material.

13. The sensor for measuring hydrogen content in metal melt according to claim 8, wherein when the reference substance is gas-phase reference substance, liquid-phase reference substance or solid-phase reference substance, the gas-phase reference substance comprises hydrogen and argon calibration gas mixtures, hydrogen and nitrogen calibration gas mixtures, hydrogen and helium calibration gas mixtures, water vapor and oxygen calibration gas mixtures or ammonia and nitrogen calibration gas mixtures, which is doped or undoped with one or more inert gases, the liquid-phase reference substance comprises lithium and lithium hydride two-phase mixture, and the solid-phase reference substance comprises yttrium hydrogen solid solution, titanium hydrogen solid solution, zirconium hydrogen solid solution or scandium hydrogen solid solution.

14. A method for measuring hydrogen content in metal melt by using the sensor for measuring hydrogen content in metal melt according to claim 8, the method comprising the following steps of:

(1) inserting the sensor and a corrosion-resistant electrode into the metal melt, and making sure that the solid proton conductor element is fully immersed into the metal melt, the quasi-electrode to be measured is in direct contact with the metal melt and the contact surface is the electrode to be measured;

(2) connecting a potentiometer and the reference electrode cable to the corrosion-resistant electrode, and measuring a potential difference between the reference electrode and the electrode to be measured, wherein when the reference substance is liquid-phase reference substance or solid-phase reference substance, the reference electrode cable penetrates through the insulating ceramic adhesive, is connected with the reference electrode and is externally connected to a measuring circuit, and the reference electrode cable is metal platinum, gold, silver, nickel-chromium alloy, iron-chromium-aluminum alloy or stainless steel; and (3) calculating the hydrogen content S of the metal melt according to the measured potential difference, a temperature of the metal melt and a saturated solubility of hydrogen in the metal melt.

* * * * *